United States Patent
Kanjilal et al.

(10) Patent No.: US 7,141,033 B2
(45) Date of Patent: Nov. 28, 2006

(54) SAMPLE COLLECTION DEVICE AND METHOD

(75) Inventors: Sagarika Kanjilal, Shoreview, MN (US); Vivek Kapur, Shoreview, MN (US)

(73) Assignee: Andx, Inc, St. Paul, MN (US)

( * ) Notice: Subject to any disclaimer, the term of this patent is extended or adjusted under 35 U.S.C. 154(b) by 0 days.

(21) Appl. No.: 11/035,662

(22) Filed: Jan. 14, 2005

(65) Prior Publication Data
US 2005/0155440 A1    Jul. 21, 2005

Related U.S. Application Data

(60) Provisional application No. 60/537,057, filed on Jan. 16, 2004.

(51) Int. Cl.
*A61M 35/00* (2006.01)

(52) U.S. Cl. .................. 604/1; 600/562; 73/863; 73/863.21; 73/863.51; 73/863.52; 73/863.81; 604/2

(58) Field of Classification Search ........... 604/1–3, 604/327–328, 330–331; 600/562–572; 73/863, 73/863.21, 215, 864.31–864.32, 864.51–864.52, 73/863.81; D10/46.2–46.3
See application file for complete search history.

(56) References Cited

U.S. PATENT DOCUMENTS

| | | | |
|---|---|---|---|
| 3,163,160 A * | 12/1964 | Cohen | 600/572 |
| 4,174,384 A | 11/1979 | Ullman et al. | |
| 4,175,008 A * | 11/1979 | White | 600/572 |
| 4,232,718 A * | 11/1980 | Wippermann | 141/358 |
| 4,312,950 A * | 1/1982 | Snyder et al. | 600/572 |
| 4,387,725 A * | 6/1983 | Mull | 600/572 |
| 4,409,988 A | 10/1983 | Greenspan | |
| 4,735,905 A * | 4/1988 | Parker | 436/174 |
| 4,789,639 A * | 12/1988 | Fleming | 436/178 |
| 5,440,942 A * | 8/1995 | Hubbard | 73/864.91 |
| 5,624,554 A * | 4/1997 | Faulkner et al. | 210/232 |
| 6,180,395 B1 * | 1/2001 | Skiffington et al. | 435/287.6 |
| 6,207,113 B1 | 3/2001 | Kagaya | |
| 6,299,842 B1 * | 10/2001 | Kozak et al. | 422/102 |
| 6,524,530 B1 * | 2/2003 | Igarashi et al. | 422/58 |
| 6,612,767 B1 * | 9/2003 | Muller | 401/130 |
| 6,653,149 B1 * | 11/2003 | Tung et al. | 436/174 |
| 6,780,160 B1 * | 8/2004 | Zhou et al. | 600/562 |
| 6,921,370 B1 * | 7/2005 | Zhou et al. | 600/562 |

FOREIGN PATENT DOCUMENTS

| | | |
|---|---|---|
| EP | 1 024 354 | 8/2000 |
| EP | 1 366 715 | 12/2003 |

\* cited by examiner

*Primary Examiner*—Tatyana Zalukaeva
*Assistant Examiner*—Keshia Gibson
(74) *Attorney, Agent, or Firm*—Brooks & Cameron, PLLC

(57) ABSTRACT

Sample collection assemblies and methods that use a collection wand having a working end and an operating end, a collection tube having a barrel portion, an assay chamber, and a partition member, with the working end of the collection wand having a scoop configured for collecting a predetermined sample volume, and with the partition member having an orifice with a boundary complementary to a cross-section of the scoop, whereby an excess of sample material can be excluded from entering the assay chamber.

18 Claims, 8 Drawing Sheets

SAMPLE COLLECTION DEVICE AND METHOD

PRIORITY DATA

This application claims priority from U.S. Provisional Application Ser. No. 60/537,057 filed Jan. 16, 2004, which is incorporated herein by reference

BACKGROUND

Devices and systems are available for collection of biological samples for analysis by known methods including immunochemistry, PCR, biochemical analysis, microbial culture, mass spectrometry, and biosensor-based detection. However, often times a particular sample collection device may be difficult to use for collecting a particular type of sample or from a particular source or for a particular type of analysis. The present invention is directed to novel sample collection devices, assemblies and methods particularly suited for collection, storage and/or analysis of a biological sample, such as fecal material, from a human or animal.

DETAILED DESCRIPTION

Figure 1:
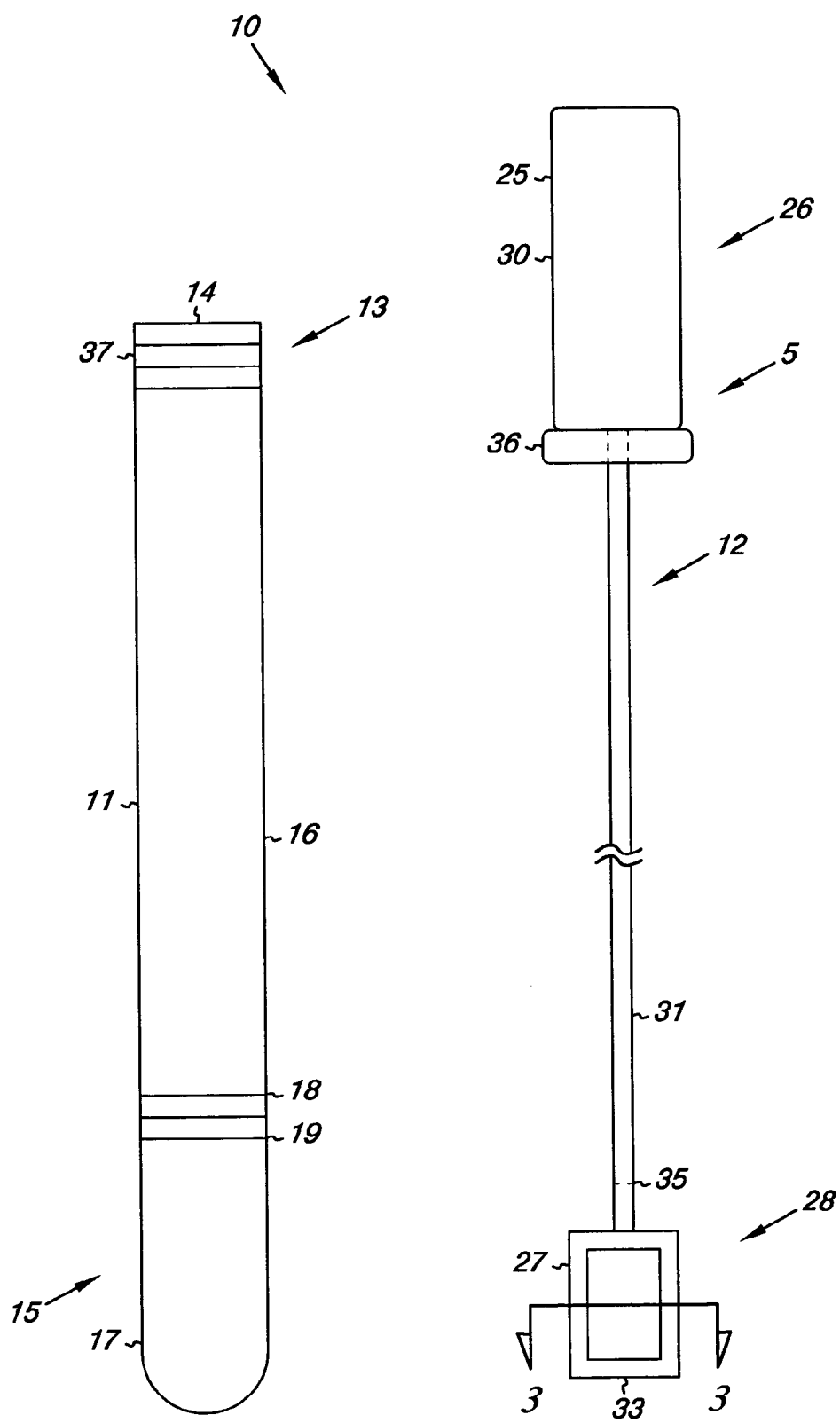
FIG. 1 is a plane view of an embodiment of a sample collection assembly according to the invention.

The present invention is directed to a sample collection assembly comprising a collection tube and collection wand. The collection tube has a barrel portion, an assay chamber and a partition member. The collection wand includes an operating end and a working end and is configured to fit within the collection tube. The operating end of the collection wand includes a handle configured for gripping and/or orientation by the operator's hand. The working end includes a collection tip suitable for collecting a measured amount of sample. A shaft can extend between the operating end and the collection tip. The shaft can be of any length appropriate for collection of the sample from a particular source. In some embodiments, the shaft can be scored or otherwise weakened to provide for separation of a portion of the shaft from the collection tip after sample collection. In some, embodiments, the shaft may have a mark or marks indicating depth of insertion for sample collection.

For descriptive purposes herein, one embodiment of a sample collection assembly of the invention will be described with reference to the figures. The illustrated embodiments may be particularly suited for collecting a fecal sample from the rectum of a horse or a production animal such as a cow, sheep or, pig or a companion animal such as a dog or a cat, or a human. Thus, according to this embodiment, the collection tip at the working end can be passed through the anus of a cow or other species and directed towards a part of the rectal wall such as the dorsal wall. Once at a desired location the handle at the operating end can be rotated to cause the collection tip to collect a fecal sample along the rectal wall, such as along the dorsal lateral wall, as the collection wand is rotated about its longitudinal axis.

In the drawings, like reference numerals represent like parts and assemblies throughout the several views. Reference to the drawings is not intended to limit the scope of the invention.

Referring to FIG. 1, a sample collection assembly 10 includes a collection tube 11 and a collection wand 12. Collection tube 11 includes a proximal end 13 having an opening 14 and a distal end 15. Collection tube 11 also includes a barrel portion 16 and assay chamber 17. In some embodiments, collection tube 11 can be scored or otherwise weakened at location 18 to provide for selective detachment of barrel portion 16 from assay chamber 17. A partition member 19 can be located near the proximal end of the assay chamber and is sealingly attached or integral with the inner perimeter of collection tube 11. If a weakened location 18 is present, partition member 19 can be located either proximal or distal thereto. The partition member 19 includes an orifice 20 for passage of the wand as will be further described below. The collection tube 11 can be manufactured from any suitable material including a polymeric material, such as plastics commonly used in the art for similar sample material collection and/or performance of analyses as will be apparent from reading the present disclosure. Examples of suitable plastics include polyurethane, polystyrene, polyvinyl, polypropylene, polyurethane, etc. Parts of the collection tube, such as a detachable barrel, may also be made of biodegradable or organic material such as card board. The sample collection assembly 10 is amenable to sterilization during or after manufacture either as an assembled unit or as separate components.

The orifice 20 of partition member 19 can be covered with a polymeric sheet or foil that preferably seals the assay chamber 17 prior to use but can be penetrated by the collection wand 12. Suitable materials for covering the orifice 20 include, for example, polymers such as poly(acrylonitrile-co-butadiene-co-styrene) polymers, acrylic polymers such as the polymethylmethacrylate, poly-n-butyl acrylate, poly(ethylene-co-acrylic acid), poly(ethylene-co-methacrylate), etc.; fluoropolymers including polytetrafluoroethylene (teflon), poly(ethylene-co-tetrafluoroethylene) copolymers, (tetrafluoroethylene-co-propylene) copolymers, polyvinyl fluoride polymers, etc., polyamides such as nylon 6, nylon 6,6, etc.; polycarbonates; polyesters such as poly(ethylene-co-terephthalate), poly(ethylene-co-1,4-naphthalene dicarboxylate), poly(butylene-co-terephthalate); polyimide materials; polyethylene materials including low density polyethylene; linear low density polyethylene, high density polyethylene, high molecular weight high density polyethylene, etc.; polypropylene, biaxially oriented polypropylene; polystyrene, biaxially oriented polystyrene; vinyl films including polyvinyl chloride. (vinyl chloride-co-vinyl acetate) copolymers, polyvinylidene chloride. polyvinyl alcohol, (vinyl chloride-co-vinylidene dichloride) copolymers, specialty films including polysulfone, polyphenylene sulfide, polyphenylene oxide, liquid crystal polyesters, polyether ketones, polyvinylbutyrl, foils; self-sealing membranes; etc. Thus, when sealed the assay chamber can be preloaded with a reagent, e.g., gas, liquid or solid material, that may be used to prepare or preserve the sample for downstream analysis. Examples of materials include glass fragmentation beads (as the same are known and understood by one of ordinary skill in the art, washing solutions, stabilizers, buffers, enzymes, etc. Embodiments of the invention, however, are not limited to these examples. One of ordinary skill in the art will appreciate other materials which may be suited for use in preparing and/or preserving the sample for downstream analysis. In some embodiments, multiple partition members may be present in the collection assembly. Some of the partition members may include the sealing material while other members may include the orifice.

In different embodiments the assay chamber 17 can serve as a container for collection and transportation of samples as well as for performance of part or all of the analysis. The assay chamber 17 can be configured for removal of the collected sample at the laboratory at the time of analysis. Alternatively, the assay chamber 17 can be sized and configured to fit within a tray or other holder that is compatible with automated sample analyzers and other laboratory equipment such as centrifuges, shakers, etc. and some or all of the analysis process steps performed directly in the chamber 17. For example, the assay chamber 17 can be sized for insertion into a multi-well (e.g., 96 well) analysis tray and the sample processed and analyzed directly in assay chamber 17. In some embodiments, the assay chamber 17 may also fit individually with standard laboratory equipment such as centrifuges, shakers, etc.

Collection wand 12 includes an operating end 25 at proximal end 26 and working end 27 at distal end 28. Operating end 25 can include a handle 30 configured to fit and /or orient with the operator's hand. A shaft 31 between operating end 25 and working end 27 can be of any length sufficient to reach the sample source. For example, if the sample source is the rectum of a cow, the shaft can be about 10 cm to 25 cm, in some embodiments, about 15 cm.

Figure 2:
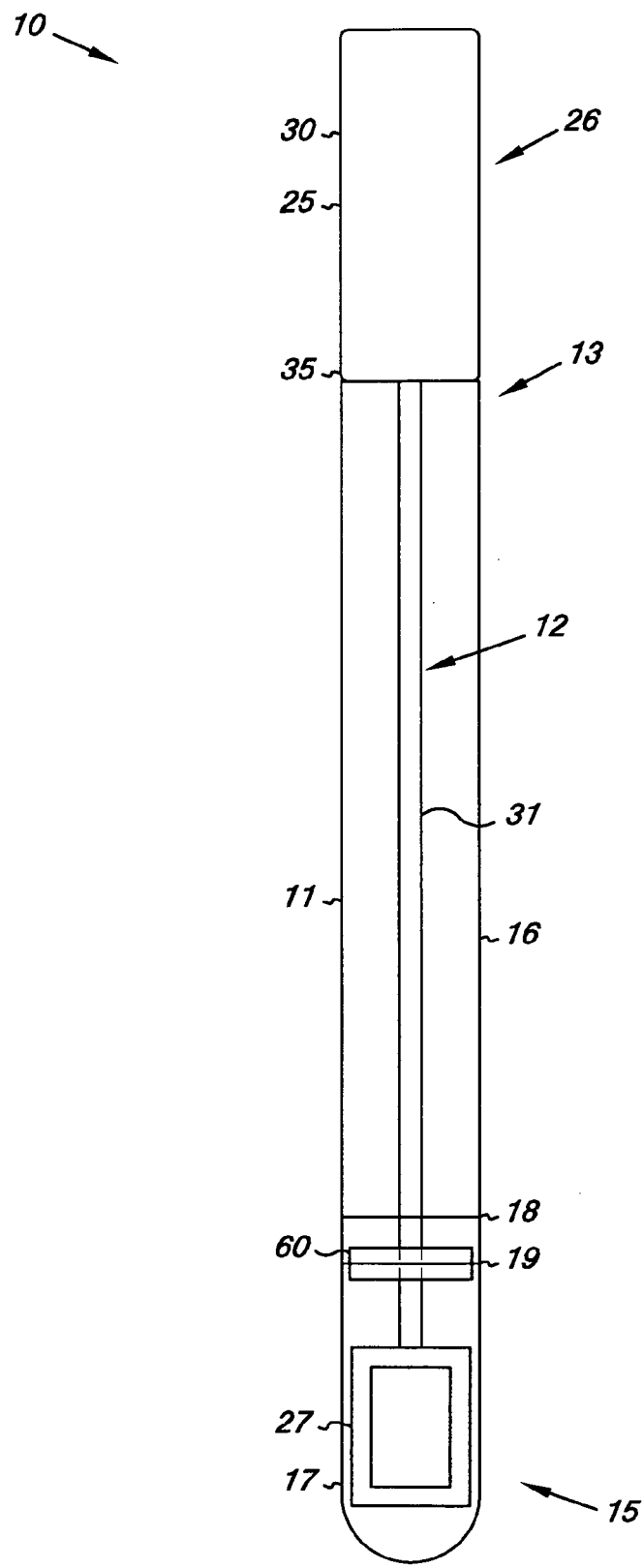
FIG. 2 is a plane view of an alternative embodiment of a sample collection assembly according to the invention.

Working end 27 can include a scoop 33 for collecting a sample. The shape and volume of scoop 33 can be sized, designed, and/or configured to collect a predetermined sample volume as suited for a particular analytical test. Shaft 31 may contain a plug (e.g., plug 60 as illustrated in FIG. 2) that sealingly fits orifice 20 of a partition member 19. Shaft 31 can be scored or otherwise weakened at location 35 to allow for selective detachment of the scoop 33 from shaft 31. The amount of force necessary for detachment of scoop 33 from shaft 31 is preferably selected to provide for ease of detachment when desired, yet not so easy that the scoop 33 inadvertently detaches during sample collection. As one of ordinary skill in the art will appreciate from reading this disclosure, various embodiments can include multiple dividers, some of which can be used for separating and sealing and/or providing additional seals for a sample to be tested. Likewise, as one will appreciate upon reading this disclosure, in the various embodiments dividers are included which function in a leveling role.

Figure 3:
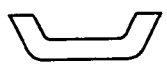
FIG. 3 is a cross sectional view through line 3—3 of a scoop according to the invention.
Figure 4:
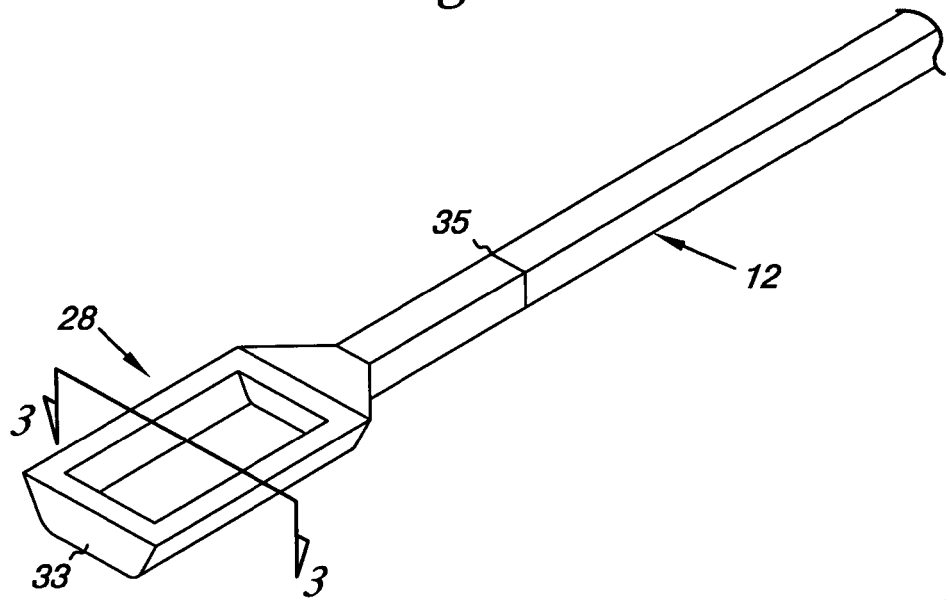
FIG. 4 is a perspective view of the working end of a collection wand according to the invention.
Figure 5:
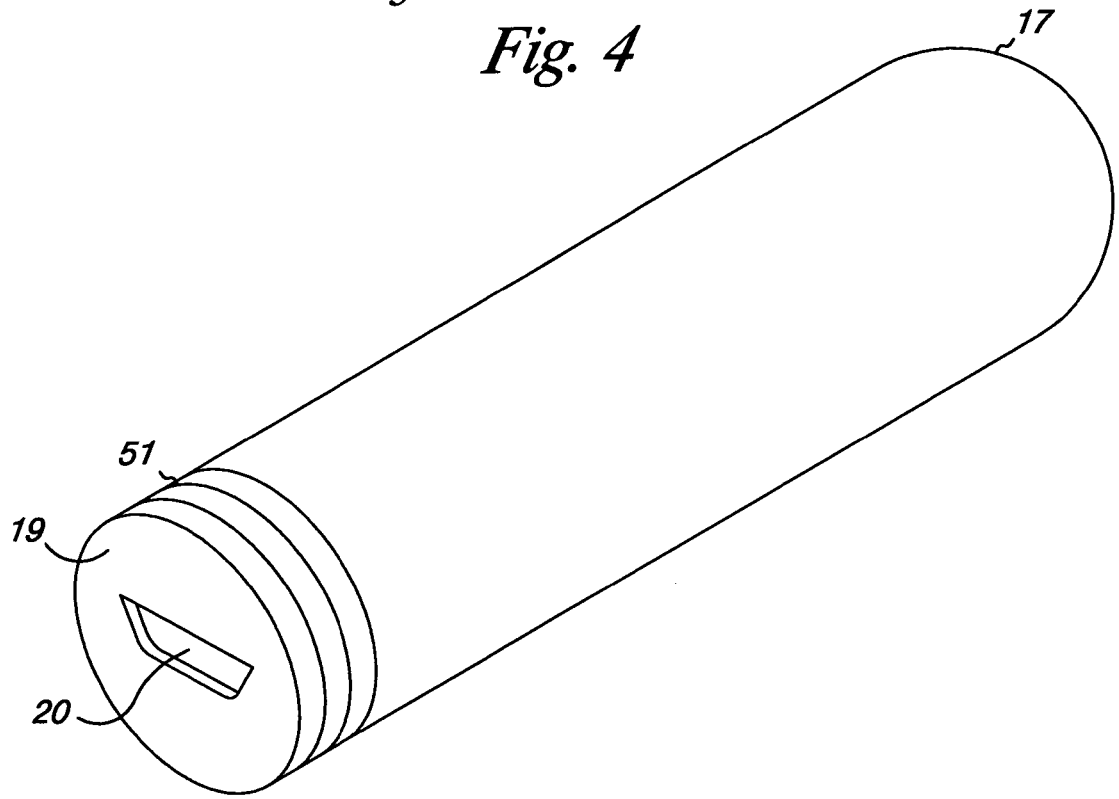
FIG. 5 is a perspective view of an assay chamber with a partition member according to the invention.

FIG. 3, is a cross sectional view through line 3—3 of scoop 33 in FIGS. 1 and 4. In preferred embodiments, the cross sectional shape of scoop is 33 is configured to have a complementary fit with the shape of orifice 20 of partition member 19 as shown in FIG. 5. The complementary fit of scoop 33 with orifice 20 provides for removal of excess sample material from the exterior surface of scoop 33. This ensures that a consistent sample size of an amount predetermined by the scoop 33 volume is delivered to the assay chamber 17.

The handle 30, shaft 31 and scoop 33 can all be manufactured from the same material. Alternatively, some or all the these components can be manufactured from different materials that are presently or later known in the art for collecting and handling samples of similar biological materials. Suitable materials for the scoop include plastics and metals. The handle and shaft can also be manufactured from plastics, metals, wood, etc. In various embodiments the scoop is manufactured from a material that facilitates removal of a sample from the scoop surface, for example, polyurethane, PTFE, high density polyethylene (HDPE), Teflon, etc.

Referring to FIG. 2, the handle 30 can have a distal end 5 configured to sealing fit within opening 14 at the proximal end 13 of collection tube 11. Alternatively, as shown in FIG. 1, a cap 36 can be located at the distal end 5 of handle 30 and include internal threads (not visible) for mating with external threads 37 if present at the proximal end of 13 of collection tube 11 or proximal end of assay tube 17. Alternatively, a separate cap 50 (shown in FIG. 6) may be used for sealing of the collection tube or the proximal end of the assay tube 17.

In use, collection wand 12 is removed from collection tube 11 and passed into the collection source, such as the rectum of an animal. The handle 30 can be rotated to facilitate collection of a fecal sample into scoop 33 as described above. After removal from the animal, the distal end 28 of wand 12 is passed through opening 14 of collection tube 11. The scoop 33 is then penetrated through orifice 20 and sealing material of one or more partition members 19 and into the assay chamber 17. After the scoop 33 passes through orifice 20, excess sample material over the predetermined scoop volume remains outside of the assay chamber.

In some embodiments the wand 12 can be inserted into the collection tube 11 with the assay chamber 17 removed. As the reader will appreciate, this will allow for the scoop to be advanced and retracted within the now open ended barrel 16 of the collection tube 11. In such embodiments, the barrel 16 will serve as a shield and/or sheath while passed into the collection source, such as the rectum of an animal. That is, in some embodiments collection wand 12 may be passed into the collection source whilst protected inside barrel 16 and the working end 27 of collection wand 12 exposed once at the site of sample collection. After a sample is collected with the tip of the working end 27 designed to collect a specific amount of sample, e.g., scoop 33, the working end 27 can be retracted into the barrel 16 and the assembly retracted from the collection source. The scoop could then be penetrated through orifice 20 and sealing material of one or more partition members 19 and into the assay chamber 17, as described above.

Referring to FIG. 2, if handle 30 has a distal end 5 configured to seal opening 14 the sample may be shipped to the lab sealed within collection tube 11. Alternatively, as shown in FIG. 1, if handle 30 includes a threaded cap 36, cap 36 can be threaded onto threads 37 on the exterior of collection tube 11 to seal the sample within collection tube 11.

Figure 6:
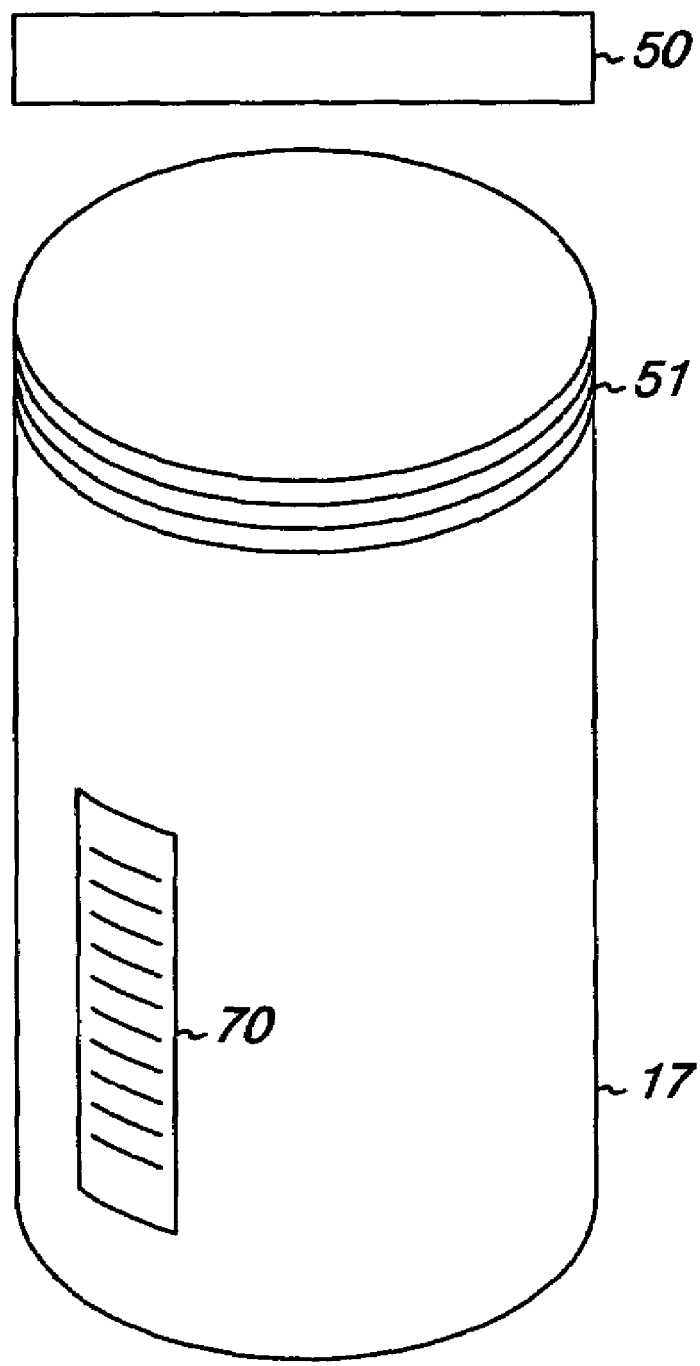
FIG. 6 is a perspective view of an embodiment of an assay chamber and cap according to the invention.

In other alternatives, some or all portions of the barrel 16 of collection tube 11 and some or all of shaft 31 of collection wand 12 can be removed and disposed. The sample can then be sealed in assay chamber 17. Referring to FIGS. 1, 3 and 4–6, in one embodiment collection tube 11 is divided at weakened location 18 leaving assay chamber 17 in a configuration such as shown in FIG. 5 or 6. As described above, a partition member 19 can be located distal to weakened location 18 and remain in assay chamber 17 (FIG. 5.) Alternatively, a partition member 19 can be located proximal to weakened area 18, and thus will not be present in assay chamber 17 (FIG. 6). In the embodiment of either FIG. 5 or 6, a cap 50 can be used to seal assay chamber 17. Cap 50 can be attached by sealing to assay chamber 17 by any suitable means, including for example internal threads (not seen) that can mate with threads 51 on the exterior of chamber 17. The scoop 33 of collection wand 12 can be separated at weakened location 35 to fit into chamber 17.

Figure 8:
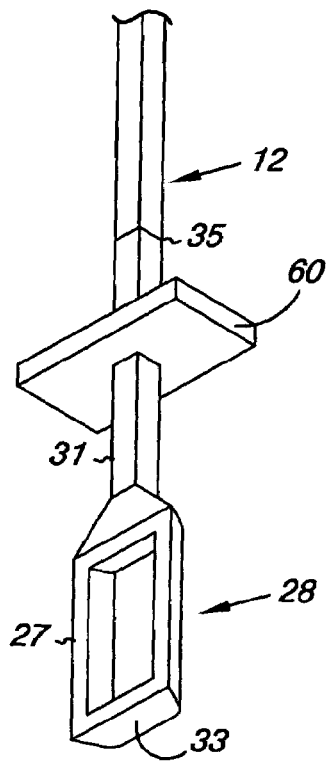
FIG. 8 is a perspective view of a portion of a collection wand according to the invention.
Figure 7:
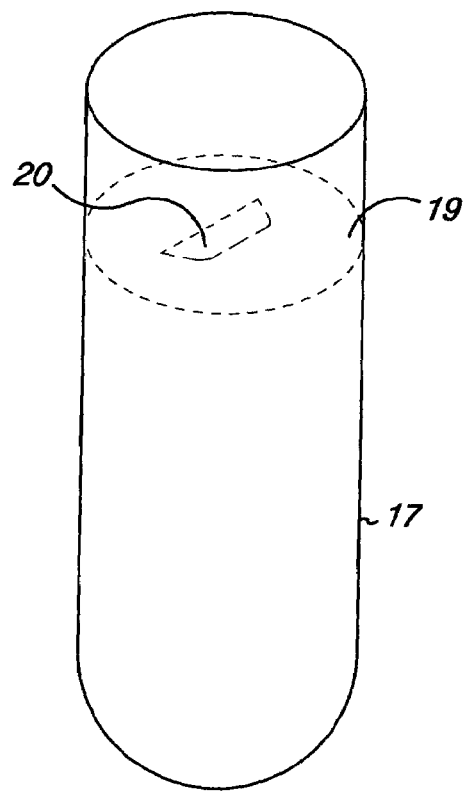
FIG. 7 is a perspective view of an embodiment of an assay chamber according to the invention.

Referring now to FIGS. 2, 7 and 8, in an alternative embodiment, collection wand 12 can include a seal plug 60 located distal to weakened location 35. According to this embodiment, partition member 19 of collection tube 11 is located distal to weakened region 18 such that after separation of barrel portion 16 from assay chamber 17, partition member 19 remains in assay chamber 17 and seal plug 60 can be force fit into orifice 20 of partition member 19 to seal assay chamber 17. After removing shaft 31 at weakened location 35, a cap 50 can be used to further seal chamber 17.

As shown in FIG. 6 the assay chamber can include a label 70 such as a bar code label, radio frequency label, or other suitable label for identifying and tracking a sample.

A sample collection device according to the invention can be used for collecting samples that can be analyzed using, for example, PCR analysis, other methods of nucleic acid-based diagnostics, immunochemistry, biochemical analysis, microbial culture, mass spectrometry, and biosensor-based detection etc. Embodiments of the invention, however, are not limited to these examples. One of ordinary skill in the art will appreciate other types of analyses which may be performed on samples collected by the sample collection device disclosed herein.

As one example, the sample collection devices herein can be advantageously used to detect bacterial organisms shed in the feces such as *Mycobacterium paratuberculosis*. The following process for detecting this organism is not meant to limit the invention, but rather to provide an example of use.

Figure 9A:
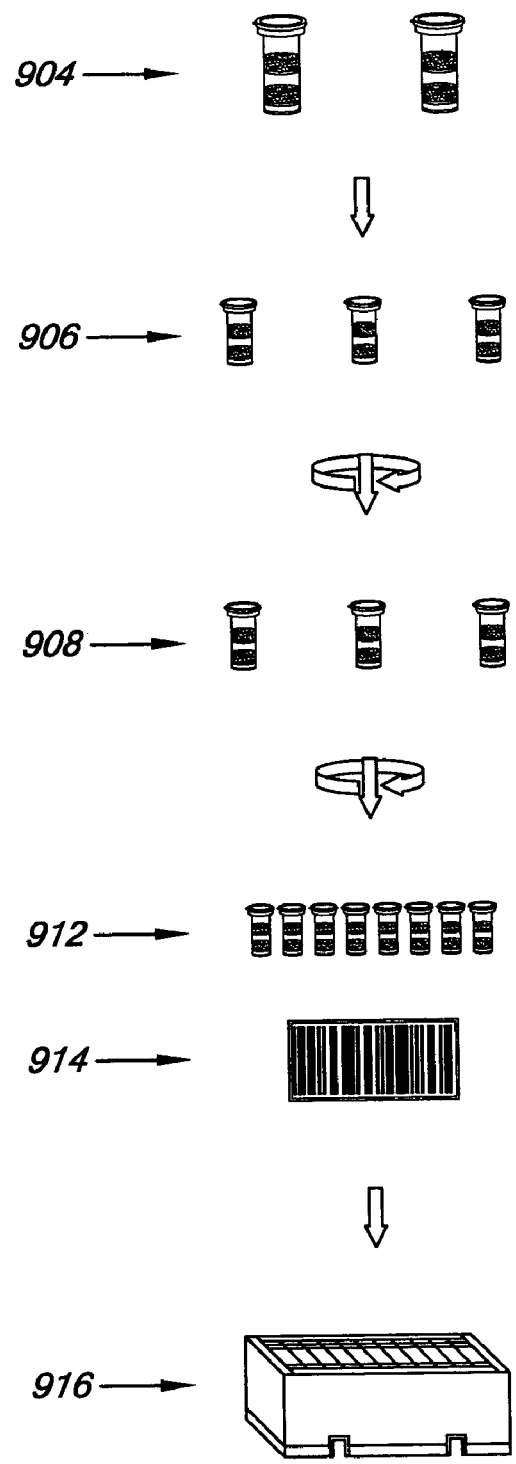
FIGS. 9A–9B illustrate an embodiment of a protocol for testing fecal samples in association with the sample collection assembly.
Figure 9B:
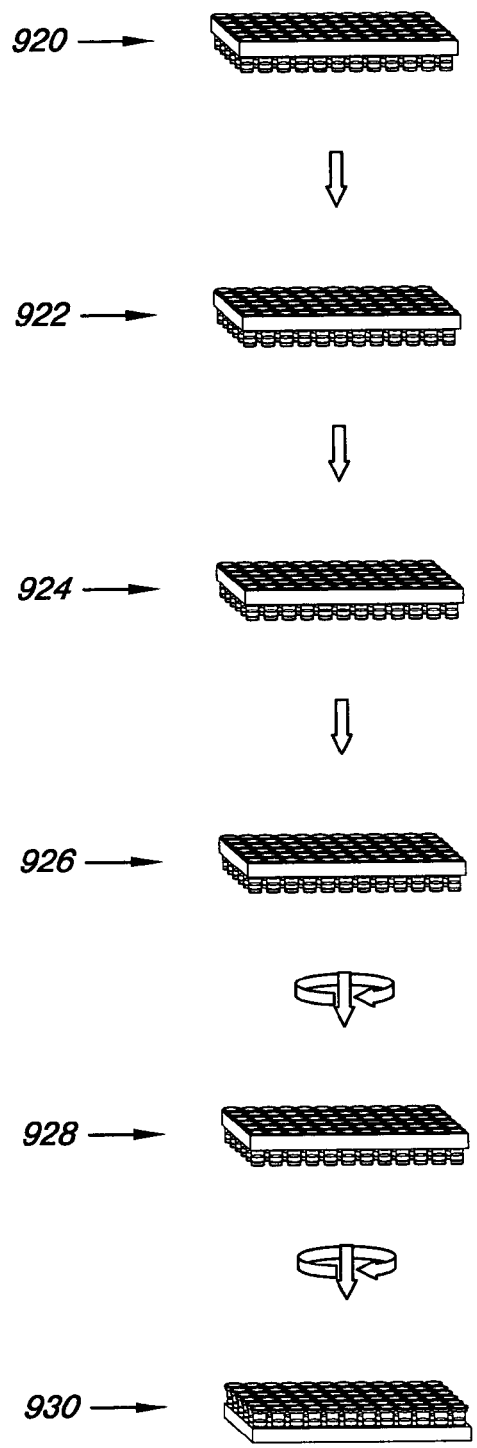

FIGS. 9A–9B illustrate an embodiment of a protocol for testing fecal samples in association with the sample collection assembly. FIGS. 9A–9B, illustrate an embodiment for a 96 sample preparation. As shown in FIG. 9A, at 904, two samples, each containing two grams or other suitable amount of fecal material, can be collected using the collection wands of two sample collection devices and individually transferred into assay chambers containing one milliliter or other suitable volume of an aqueous solution, such as a buffer or laboratory water. Next, the two samples can be shaken, for example, shaken for thirty minutes. As shown at 906, each of the two samples can be further divided into three test tubes containing additional solutions. In each of the resulting samples ten five millimeter beads can be added and the samples can be subjected to a bead beater, e.g., for five minutes. The sample can further be placed in a centrifuge for five minutes at 1000×g at four degrees Celsius. One point four milliliters of supernatant from each tube can be transferred into corresponding fresh tubes containing 0.6 milliliters ASL buffer and 250 milligrams of 0.1 millimeter beads (as shown at 908). The samples can be incubated at 70 degrees Celsius for thirty minutes and placed, once again, in a bead beater, e.g., for another five minutes, and once again be placed in a centrifuge for five minutes at 1000×g at four degrees Celsius. As shown at 912, samples can be further processed in a QIAamp 96 DNA Blood BioRobot kit such as in a BioRobot 9604. For example, tubes containing the samples can be placed eight to a bar and a number of bars may be batch processed at one time. At 914 a suitable mechanism can be employed for identifying and tracking the samples, e.g., scanning bar codes. As shown at 916, 400 micro liters of supernatant from the samples can be transferred from each of tube and arranged as twelve bars of eight to the corresponding wells of a 96-well block and further undergo Aliquoting of QIAGEN protease, e.g., 40 micro liters per well, and 400 micro liters of a lysis buffer, e.g., AL, can be added. Further, the samples can undergo incubation at 70 degrees Celsius for thirty minutes in a thermoblock.

In FIG. 9B at 920 400 micro liters of ethanol can be added and the samples transferred. A first overlay of 650 micro liters of lysate to QIAamp 96 plate is performed and the samples subjected to a vacuum for three minutes. The remaining lysate can be transferred with 310 micro liters of Buffer AW1. The samples can be subjected to a vacuum for another seven minutes. At 922, the samples can undergo a first wash with 310 micro liters of Buffer AW1. The samples can be subjected to a vacuum for another five minutes. At 924, the samples can undergo a second wash with 1000 micro liters of Buffer AW2. The samples can be subjected to a vacuum for another two minutes. At 926, the samples can undergo a third wash with 1,100 micro liters of Buffer AW2. The samples can be subjected to a vacuum for another two minutes. The samples can be placed in a centrifuge for ten minutes at 5,700×g to dry. At 928, 100 micro liters of $dH_2O$ can be added to the samples and the samples can be incubated fifteen minutes with shaking at room temperature. The samples can be placed in a centrifuge for three minutes at 5,700×g to elute. according to this exemplary embodiment, the samples are then ready to use as DNA samples as shown at 930.

Figure 10:
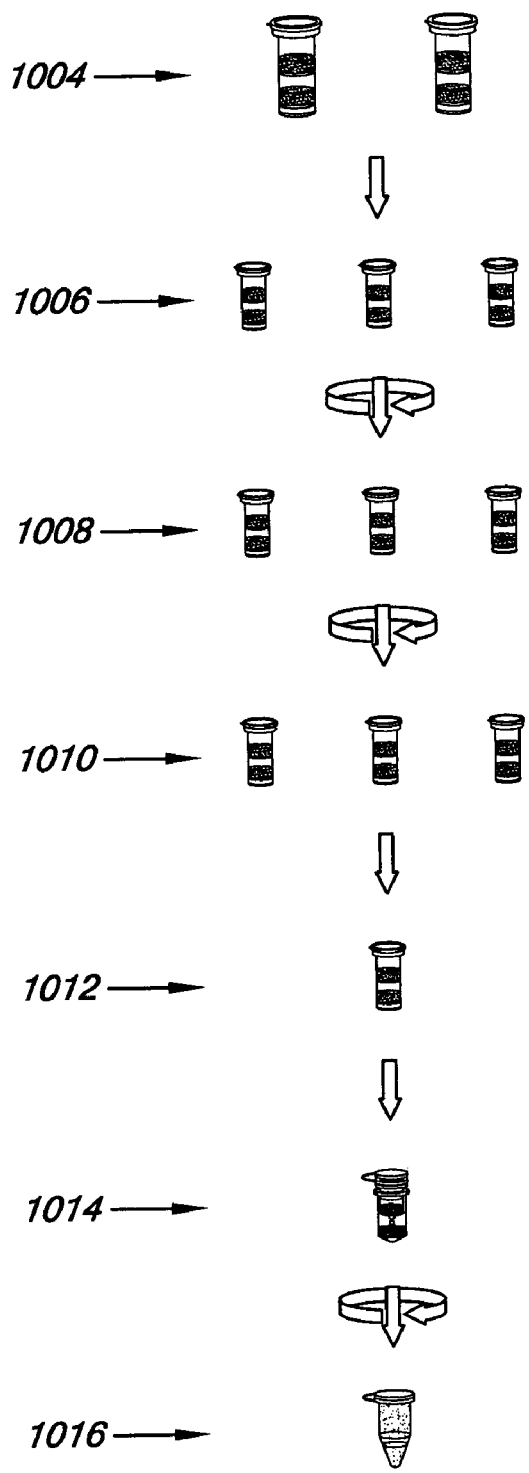
FIG. 10 illustrates another embodiment of a protocol for testing fecal samples in association with the sample collection assembly.

FIG. 10 illustrates another embodiment of a protocol for testing fecal samples in association with the sample collection assembly. FIG. 10 illustrates an embodiment for a single sample preparation. As shown in FIG. 10, this exemplary testing protocol embodiment in association with the sample collection assembly includes collection of two samples, each containing two grams of fecal material, using the collection wands of two sample collection devices and individually transferring the samples into assay chambers containing one milliliter of an aqueous solution. After transportation to the laboratory, as shown at 1004, water of a buffer containing salts and/or enzymes to dilute to a specified amount, e.g., 2 fold, etc., can be added. The two samples can be agitated to mix thoroughly for a given period of time, e.g., thirty minutes. Stage 1006 illustrates continuing to process the sample or aliquot material, e.g., into three replicate tubes. A specified number, e.g., ten, beads of silica, zirconium, or a combination of glass and or metal having a specified diameter, e.g., five millimeters, can be added. The samples can be agitated using a manual or robotic device, e.g., bead beater or mixer mill, for a specified period of time, e.g., five minutes. The sample can further be placed in a centrifuge for a specified period of time, temperature and relative centrifugal force, e.g., 1000×g at four degrees Celsius for five minutes. At 1008 a given amount of supernatant, e.g., 1.4 milliliters, can be added to a specified volume, e.g., 0.6 milliliters of a solubalization buffer, e.g., ASL. Further 250 milligrams of 0.1 millimeter beads, e.g., silica or zirconium can be added. At 1010 the samples can once again be agitated with a bead beater, e.g., for another five minutes and incubated at 70 degrees Celsius for thirty minutes. The sample can once again be placed in a centrifuge for five minutes at 1000×g at four degrees Celsius. At 1012, one can prepare DNA using methods that are familiar to one of ordinary skill in the art or using a specified kit, e.g., Qiagen blood kit. 200 micro liters of supernatant along with 20 micron liters of PK and 200 micro liters of a buffer, e.g., AL, can be added. Further, the sample can undergo incubation at 70 degrees Celsius for thirty minutes. As shown at 1014 a washing step may be performed using Ethanol and buffers AW1, AW2, etc. The sample can again undergo a centrifuge for three minutes at 6000×g. According to this exemplary embodiment, the sample is then ready to use for DNA sampling as shown at 1016.

In other embodiments, the protocols may be simplified, e.g., steps may be omitted, centrifugation used instead of vacuum, and other volumes, buffers, or g forces used. Different portions of the protocol may also be performed at different sites with some steps being accomplished at the collection location, e.g., an animal production facility such as a dairy farm, some steps being accomplished during transportation, and others at a facility such as a laboratory where the sample has been transported to.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of the embodiments of the invention. It is to be understood that the above description has been made in an illustrative fashion, and not a restrictive one. Combination of the above embodiments, and other embodiments not specifically described herein will be apparent to those of skill in the art upon reviewing the above description. The scope of the various embodiments of the invention includes any other applications in which the above structures and methods are used. Therefore, the scope of various embodiments of the invention should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby

What is claimed is:

1. A sample collection assembly comprising:
   a collection wand having a working end, and an operating end;
   a collection tube having a barrel portion, an assay chamber, and a partition member;
   wherein the working end of the collection wand has a scoop configured for collecting a predetermined sample volume; and
   wherein the partition member has an orifice with a boundary complementary to a cross-section of the scoop, the partition member and scoop are configured such that an excess of sample material is excluded from entering the assay chamber when passing the scoop through the orifice;
   wherein a shaft with a weakened location extends between the working end and the operating end and includes a sealing arrangement for sealing the assay chamber distal from the weakened location and proximal to the partition member;
   wherein the assay chamber is detachable with the scoop therein in a sealed configuration; and
   wherein the assembly is configured such that detaching the assay chamber from the collection tube causes the shaft to detach at the weakened location.

2. The sample collection assembly of claim 1 wherein the barrel of the collection tube is detachable from the assay chamber.

3. The sample collection assembly of claim 1 wherein the partition member includes an orifice configured for snug passage of the working end therethrough.

4. The sample collection assembly of claim 1 further including a sealing arrangement for sealing the assay chamber.

5. The sample collection assembly of claim 4 wherein the barrel portion is detachable from the assay chamber and the sealing arrangement comprises a plug configured to seal the orifice of the partition member.

6. The sample collection assembly of claim 1 wherein the assay chamber is adapted for transportation, processing, and analysis of a sample.

7. The sample collection assembly of claim 6 wherein the assay chamber is adapted to be pre-sealed with a reagent therein as useful to transportation, processing, and analysis of the sample.

8. The sample collection assembly of claim 6 wherein the assay chamber is adapted to be detached and interfaced with other standard laboratory equipment individually or in multi-well formats.

9. The sample collection assembly of claim 1 wherein the working end is adapted to be inserted in body cavities of biological entities including humans and animals for collection of biological samples.

10. The sample collection assembly of claim 9 wherein the working end is adapted to be inserted through an anus for collection of feces and samples from regions of a gastrointestinal tract.

11. The sample collection assembly of claim 1 wherein the working end and the assay chamber are adapted to collect, transport, and assay infectious agents.

12. The sample collection assembly of claim 11 wherein the infectious agents include infectious agents present in host species including humans and animals.

13. The sample collection assembly of claim 12 wherein the working end and the assay chamber are adapted to collect, transport, and analyze sample for detection and diagnosis of *Mycobacterium avium* subspecies paratuberculosis.

14. The sample collection assembly of claim 11 wherein the working end and the assay chamber are adapted to collect, transport, and analyze samples with application in biodefense.

15. The sample collection assembly of claim 1 wherein the collection wand includes a shaft separating the working end from the operating end, the shaft having a length suited to reach a particular sample source.

16. The sample collection assembly of claim 1 wherein the assay chamber is preloaded with at least one reagent, used to process the sample material for analysis, from a group that includes glass fragmentation beads, washing solutions, stabilizers, buffers, and enzymes.

17. A sterile sample collection assembly, comprising:
   an apparatus configured to collect a measured amount of a sample and to process the sample for analysis, including:

a working end of a wand having a scoop configured for collecting a predetermined sample volume; and a partition member having an orifice with a boundary complementary to a cross-section of the scoop, the partition member and scoop are configured such that an excess of sample material can be excluded from entering an assay chamber when passing the scoop through the orifice; and wherein a shaft with a weakened location extends between the working end and the operating end and includes a sealing arrangement for sealing the assay chamber distal from the weakened location and proximal to the partition member;

wherein the assay chamber is detachable with the scoop therein in a sealed configuration; and wherein the assembly is configured such that detaching the assay chamber from the collection tube causes the shaft to detach at the weakened location.

18. A sample collection assembly, comprising:

an apparatus configured to collect, transport, and assay samples for diagnosis of *Mycobacterium avium* subspecies paratuberculosis, including:

a working end of a wand having a scoop configured for collecting a predetermined sample volume; and a partition member having an orifice with a boundary complementary to a cross-section of the scoop, the partition and scoop are configured such that an excess of sample material can be excluded from entering an assay chamber when passing the scoop through the orifice;

wherein a shaft with a weakened location extends between the working end and the operating end and includes a sealing arrangement for sealing the assay chamber distal from the weakened location and proximal to the partition member;

wherein the assay chamber is detachable with the scoop therein in a sealed configuration; and wherein the assembly is configured such that detaching the assay chamber from the collection tube causes the shaft to detach at the weakened location.

* * * * *